US009241609B2

(12) United States Patent
Navok et al.

(10) Patent No.: US 9,241,609 B2
(45) Date of Patent: Jan. 26, 2016

(54) METHOD AND APPARATUS FOR CONVERSION OF SIGNALS FROM A FIRST TYPE OF IMAGE SENSOR TO A SECOND TYPE OF CAMERA CONTROL UNIT

(75) Inventors: Ezra Navok, Stamford, CT (US); Shai Finkman, Haifa (IL); Christopher A. Cook, New York, NY (US)

(73) Assignee: Gyrus ACMI, Inc., Southborough, MA (US)

( * ) Notice: Subject to any disclaimer, the term of this patent is extended or adjusted under 35 U.S.C. 154(b) by 494 days.

(21) Appl. No.: 13/605,190

(22) Filed: Sep. 6, 2012

(65) Prior Publication Data
US 2014/0063217 A1 Mar. 6, 2014

(51) Int. Cl.
| | |
|---|---|
| A61B 1/05 | (2006.01) |
| A61B 1/00 | (2006.01) |
| H04N 7/18 | (2006.01) |
| H04N 5/225 | (2006.01) |
| A61B 1/045 | (2006.01) |
| A61B 1/04 | (2006.01) |
| H04N 5/232 | (2006.01) |

(52) U.S. Cl.
CPC ......... *A61B 1/00006* (2013.01); *A61B 1/00009* (2013.01); *H04N 5/2253* (2013.01); *H04N 7/185* (2013.01); *H04N 5/23209* (2013.01); *H04N 2005/2255* (2013.01)

(58) Field of Classification Search
USPC .................. 348/72, 572, 573, 222.1, E7.087, 348/E7.085; 375/240.01; 341/108
See application file for complete search history.

(56) References Cited

U.S. PATENT DOCUMENTS

| | | | |
|---|---|---|---|
| 4,706,118 A | 11/1987 | Kato et al. | |
| 6,387,043 B1 | 5/2002 | Yoon | |
| 7,453,490 B2 * | 11/2008 | Gunday | 348/68 |
| 7,471,310 B2 * | 12/2008 | Amling | A61B 1/00059 348/211.14 |
| 7,787,030 B2 | 8/2010 | Fridrich et al. | |
| 7,833,152 B2 | 11/2010 | Chatenever et al. | |
| 8,550,990 B2 | 10/2013 | Seto et al. | |
| 9,080,992 B2 * | 7/2015 | Olsson | H04N 5/2252 |
| 2001/0009438 A1 * | 7/2001 | Kihara | H04N 9/735 348/223.1 |
| 2004/0201686 A1 * | 10/2004 | Amling | A61B 1/00059 348/207.1 |
| 2005/0259178 A1 * | 11/2005 | Takahashi | 348/363 |
| 2006/0114986 A1 * | 6/2006 | Knapp, II | A61B 1/00103 375/240.01 |
| 2006/0258951 A1 * | 11/2006 | Bleich et al. | 600/546 |
| 2007/0002134 A1 | 1/2007 | Ishihara et al. | |

(Continued)

FOREIGN PATENT DOCUMENTS

| | | | |
|---|---|---|---|
| JP | 2001358998 | 12/2001 | |
| WO | WO 2010123858 A2 * | 10/2010 | A61B 1/00016 |

*Primary Examiner* — Christopher S Kelley
*Assistant Examiner* — Kathleen Walsh
(74) *Attorney, Agent, or Firm* — Chapin IP Law, LLC.

(57) ABSTRACT

A method and apparatus for conversion of signals from a first type of image sensor to a second type of camera control unit is presented. A first interface is provided for enabling electrical communication between the conversion module and an image sensor, the image sensor being interchangeable between a Complimentary Metal Oxide Semiconductor (CMOS) and a Charge Coupled Device (CCD) image sensor. A second interface is provided for enabling electrical communication between the conversion module and a camera control unit (CCU). Also provided is conversion circuitry in communication with the first interface and the second interface, the conversion circuitry receiving signals of a first type from the first interface, converting the signals of a first type to signals of a second type and providing the signals of a second type to the second interface.

21 Claims, 4 Drawing Sheets

(56) References Cited

U.S. PATENT DOCUMENTS

| | | | |
|---|---|---|---|
| 2008/0008301 A1* | 1/2008 | Huang | 379/93.07 |
| 2008/0084487 A1* | 4/2008 | Yoshida | 348/243 |
| 2009/0135245 A1 | 5/2009 | Luo et al. | |
| 2010/0013928 A1 | 1/2010 | Haug | |
| 2010/0033604 A1* | 2/2010 | Solomon | G02B 27/0025 348/241 |
| 2010/0069713 A1 | 3/2010 | Endo et al. | |
| 2011/0037876 A1 | 2/2011 | Talbert et al. | |
| 2011/0140003 A1* | 6/2011 | Beck | A61B 1/00057 250/459.1 |
| 2011/0149057 A1* | 6/2011 | Beck | A61B 1/00057 348/65 |
| 2011/0149084 A1* | 6/2011 | Beck | A61B 1/00057 348/187 |
| 2011/0238977 A1 | 9/2011 | Talbert et al. | |
| 2012/0075443 A1* | 3/2012 | Rovegno | 348/65 |

* cited by examiner

```
┌─────────────────────────────────────────────────────────┐
│  WHEN THE FIRST INTERFACE ENABLES ELECTRICAL COMMUNICATION │
│  BETWEEN THE CONVERSION MODULE AND A CHARGE COUPLED DEVICE │
│    (CCD) IMAGE SENSOR, THE SIGNALS OF A FIRST TYPE COMPRISE │
│      ANALOG SIGNALS AND WHEREIN WHEN THE SECOND INTERFACE  │
│     ENABLES ELECTRICAL COMMUNICATION BETWEEN THE CONVERSION │
│        MODULE AND A COMPLIMENTARY METAL OXIDE SEMICONDUCTOR │── 214
│         (CMOS) CCU, THE SIGNALS OF A SECOND TYPE COMPRISE DIGITAL │
│           SIGNALS; AND WHEREIN WHEN THE FIRST INTERFACE ENABLES │
│         ELECTRICAL COMMUNICATION BETWEEN THE CONVERSION MODULE │
│  AND A COMPLIMENTARY METAL OXIDE SEMICONDUCTOR (CMOS) IMAGE │
│    SENSOR, THE SIGNALS OF A FIRST TYPE COMPRISE DIGITAL SIGNALS; │
│      AND WHEREIN WHEN THE SECOND INTERFACE ENABLES ELECTRICAL │
│   COMMUNICATION BETWEEN THE CONVERSION MODULE AND A CHARGE │
│        COUPLED DEVICE (CCD) CCU, THE SIGNALS OF A SECOND TYPE │
│                       COMPRISE ANALOG SIGNALS              │
└─────────────────────────────────────────────────────────┘
                              │
                              ▼                              ── 216
┌─────────────────────────────────────────────────────────┐
│        THE CONVERTING IS PERFORMED BY CONVERSION CIRCUITRY │
│          COMPRISING AN ANALOG-TO-DIGITAL (A/D) CONVERTER IN │
│       COMMUNICATION WITH THE FIRST INTERFACE AND THE SECOND │
│      INTERFACE;TIMING CIRCUITRY IN COMMUNICATION WITH THE A/D │
│     CONVERTER AND THE FIRST INTERFACE; AND POWER CIRCUITRY FOR │
│      PROVIDING POWER TO THE A/D CONVERTER, THE TIMING CIRCUITRY │
│                        AND THE FIRST INTERFACE             │
└─────────────────────────────────────────────────────────┘
                              │
                              ▼                              ── 218
┌─────────────────────────────────────────────────────────┐
│         THE CONVERTING IS PROVIDED BY CONVERSION CIRCUITRY │
│            COMPRISING A DIGITAL-TO-ANALOG (D/A) CONVERTER IN │
│        COMMUNICATION WITH THE FIRST INTERFACE AND THE SECOND │
│       INTERFACE; TIMING CIRCUITRY IN COMMUNICATION WITH THE D/A │
│     CONVERTER AND THE FIRST INTERFACE; ANDPOWER CIRCUITRY FOR │
│       PROVIDING POWER TO THE D/A CONVERTER, THE TIMING CIRCUITRY │
│                        AND THE FIRST INTERFACE             │
└─────────────────────────────────────────────────────────┘
                              │
                              ▼
┌─────────────────────────────────────────────────────────┐
│         THE CONVERTING IS PROVIDED BY CONVERSION CIRCUITRY │
│          COMPRISING AN ANALOG-TO-DIGITAL (A/D) CONVERTER IN │
│       COMMUNICATION WITH THE FIRST INTERFACE AND THE SECOND │── 220
│            INTERFACE; A DIGITAL-TO-ANALOG (D/A) CONVERTER IN │
│        COMMUNICATION WITH THE FIRST INTERFACE AND THE SECOND │
│      INTERFACE; TIMING CIRCUITRY IN COMMUNICATION WITH THE A/D │
│        CONVERTER, THE D/A CONVERTER AND THE FIRST INTERFACE; AND │
│      POWER CIRCUITRY FOR PROVIDING POWER TO THE A/D CONVERTER, │
│         THE D/A CONVERTER , THE TIMING CIRCUITRY, AND THE FIRST │
│                              INTERFACE                     │
└─────────────────────────────────────────────────────────┘
```

FIGURE 3B

METHOD AND APPARATUS FOR CONVERSION OF SIGNALS FROM A FIRST TYPE OF IMAGE SENSOR TO A SECOND TYPE OF CAMERA CONTROL UNIT

BACKGROUND

Endoscopic surgery is a minimally invasive surgical procedure that is used to analyze the interior of a body cavity or interior surfaces of an organ by inserting a tubular member into the body cavity through a minimal incision. A conventional endoscope (sometimes referred to herein simply as a "scope") is generally an instrument with an image sensor for visualizing the interior of a body cavity. A wide range of applications have been developed for the general field of endoscopes including, but not necessarily limited to; arthroscope, angioscope, bronchoscope, choledochoscope, colonoscope, cytoscope, duodenoscope, enteroscope, esophagogastro-duodenoscope (gastroscope), laparoscope, laryngoscope, nasopharyngo-neproscope, sigmoidoscope, thoracoscope, and utererscope (hereinafter referred to generally as "endoscope"). The advantages of endoscopic surgery include smaller surgical incisions and less soft tissue damage. As a result, there is significantly less discomfort and pain for the patient as well as a decrease in recovery time.

As part of forming an image of the surgical site, the endoscope includes an image sensor. Endoscopes may also incorporate a light source and one or more tubular members for observation or operation within the body, such as a working channel for passing diagnostic, monitoring, treatment, or surgical tools through the endoscope. An endoscopic system typically includes an image sensor (e.g. a camera) coupled to a camera control unit (CCU). The CCU captures and processes video signals from the image sensor for display on a monitor, as well as for transfer to existing recording and printing devices. The image sensor typically communicates with the CCU by way of a cable.

Image sensor processing circuitry is configured for either a Complimentary Metal Oxide Semiconductor (CMOS) image sensor or a Charge Coupled Device (CCD) image sensor. CCU circuitry is typically hard wired for the specific type of sensor it was designed to work with. It is not possible with commercial systems to interchange a CCD sensor into a CCU designed to work with a CMOS sensor or to interchange a CMOS sensor into a CCU designed to work with a CCD sensor. A CCD sensor output is an analog signal whereas a CMOS sensor output is typically a digital signal. The different types of sensors require considerably different support and interface circuitry. The additional complexity of developing a CCU that would handle both types of sensors has prevented this from becoming commercially feasible.

SUMMARY

Conventional mechanisms such as those explained above suffer from a variety of deficiencies. One such deficiency is that CMOS cameras cannot be used with existing CCD systems, and that CCD cameras cannot be used with exiting CMOS systems. Image sensor processing circuitry is configured for either a CMOS image sensor or a CCD image sensor. A camera control unit (CCU) circuitry is hard wired for the specific type of sensor. It is not possible with commercial systems to interchange a CCD sensor into a CCU designed to work with a CMOS sensor or to interchange a CMOS sensor into a CCU designed to work with a CCD sensor. A CCD sensor output is an analog signal whereas a CMOS sensor output is typically a digital signal. The different types of sensors require considerably different support and interface circuitry. The additional complexity of developing a CCU that would handle both types of sensors has prevented this from becoming commercially feasible.

Embodiments of the invention significantly overcome such deficiencies and provide mechanisms and techniques that provide a conversion module that allows a CMOS camera to be used with an existing CCD system or allow a CCD camera to be used with an existing CMOS system.

The presently disclosed method and apparatus for conversion of signals from a first type of image sensor to a second type of camera control unit includes utilization of a conversion module that allows a CCD image sensor to be used with a CMOS based CCU, and a CMOS image sensor to be used with a CCD based CCU. The module circuitry allows direct substitution of a CCD sensor in a CMOS based CCU imaging products and a CMOS sensor into existing CCD based products. In a particular embodiment of a method for providing conversion that allows a CMOS camera to be used with an existing CCD system or allows a CCD camera to be used with an existing CMOS system, the method includes receiving, at a first interface of a conversion module, signals of a first type, the first interface capable of electrical communication with an image sensor, wherein the image sensor is interchangeable between a Complimentary Metal Oxide Semiconductor (CMOS) and a Charge Coupled Device (CCD) image sensor. The method further includes converting the signals of a first type to signals of a second type. Additionally, the method includes providing the signals of a second type to a second interface, the second interface capable of being in electrical communication with a Camera Control Unit (CCU).

It is to be understood that the embodiments of the invention can be embodied strictly as a software program, as software and hardware, or as hardware and/or circuitry alone, such as within a conversion module. The features of the invention, as explained herein, may be employed in endoscope systems and/or software for such systems.

Note that each of the different features, techniques, configurations, etc. discussed in this disclosure can be executed independently or in combination. Accordingly, the present invention can be embodied and viewed in many different ways. Also, note that this summary section herein does not specify every embodiment and/or incrementally novel aspect of the present disclosure or claimed invention. Instead, this summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

BRIEF DESCRIPTION OF THE DRAWINGS

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 3A and 3B illustrate a flow diagram of a particular embodiment of a method for providing conversion that allows a CMOS camera to be used with an existing CCD system or allows a CCD camera to be used with an existing CMOS system in accordance with embodiments of the invention.

DETAILED DESCRIPTION

Figure 1:
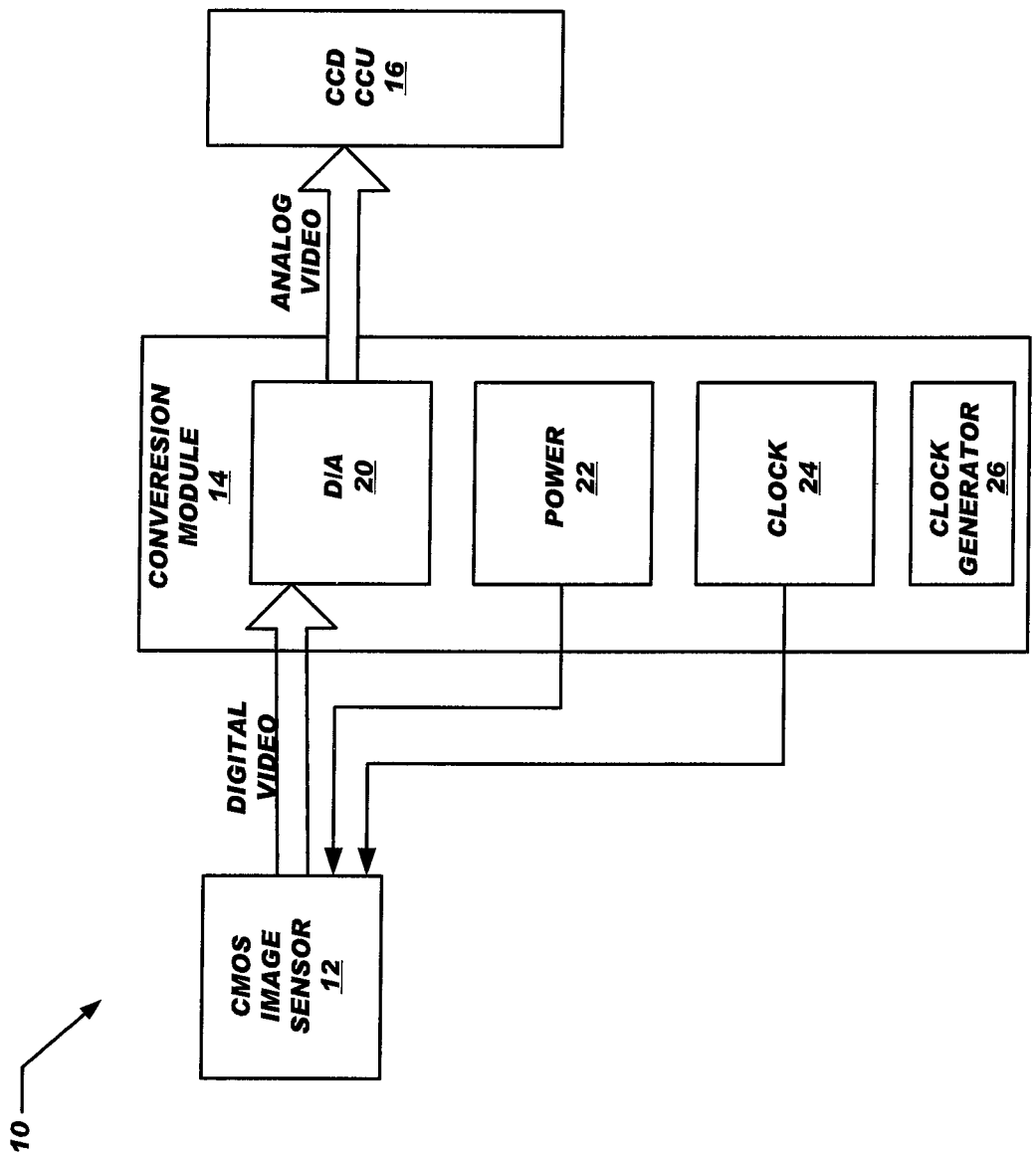
FIG. 1 is a block diagram of a conversion module for a CMOS image sensor and a CCD-based CCU in accordance with embodiments of the invention.

The presently disclosed method and apparatus for conversion of signals from a first type of image sensor to a second type of camera control unit includes utilization of a conversion module that allows a CCD image sensor to be used with a CMOS based CCU, and a CMOS image sensor to be used with a CCD based CCU. Currently there are many endoscopes and systems that are solely CCD based or solely CMOS based. The presently described method and apparatus will enable both CCD and CMOS based endoscopes and devices to use either CCD or CMOS CCUs. The present invention will also facilitate the conversion, through redesign, of CCD based scopes to CMOS image sensors, which will result in saving money.

The conversion module is comprised of electronic circuitry and firmware. In one particular embodiment the conversion module comprises a box or a wired module that provides an input port for an imaging product (e.g., a CCD endoscope) and an output port that would provide a signal appropriate to supply directly to a vision system (e.g. a CMOS CCU). The conversion module includes electronic circuitry to provide power supply voltages and to generate clock, timing, and control signals for the image sensor. The conversion module utilizes additional circuitry to process the signals from the image sensor and convert these to a format suitable for the intended CCU.

In the case of a CMOS sensor, a Digital to Analog (D/A) converter would be required to produce the analog signal needed for a CCD type CCU. A DAC (Digital to Analog Converter) converts an abstract finite-precision number (usually a fixed-point binary number) into a physical quantity (e.g., a voltage or a pressure). In particular, DACs are often used to convert finite-precision time series data to a continually varying physical signal. A typical DAC converts the digital signals into a sequence of impulses that are then processed by a reconstruction filter using some form of interpolation to fill in data between the impulses. Other DAC methods (e.g., methods based on delta-sigma modulation) produce a pulse-density modulated signal that can then be filtered in a similar way to produce a smoothly varying signal.

In the case of a CCD sensor, an A/D converter would be utilized to provide digital data required by a CMOS CCU. An A/D converter is a device that uses sampling to convert a continuous quantity to a discrete time representation in digital form. The digital output may use different coding schemes. Typically the digital output will be a two's complement binary number that is proportional to the input.

In a first embodiment the conversion module includes direct, hard-wired circuitry designed for a specific sensor and CCU. There are also additional embodiments wherein the conversion module has greater capabilities that could convert a wider range of sensor formats for multiple controller versions. This could be done with a hard-wired Field Programmable Gate Array (FPGA) or a microcontroller and associated firmware. A further embodiment of the conversion module would be able to detect the sensor and CCU type and automatically setup power supply, timing, clock, and data stream formatting for a sensor to suit the CCU that the conversion module was coupled to. This would require a more sophisticated controller and additional firmware. In tone form, the conversion module would include a power supply, clock, and A/D or D/A converter. More general versions would include interface circuitry, a controller and firmware for determining sensor type and format, a controller and firmware for determining CCU type and format, and circuitry or a controller to process and format the data stream accordingly.

Referring now to FIG. 1, a first environment 10 including the use of a conversion module 14 as part of an endoscopic system is shown. A CMOS image sensor 12 is shown coupled to conversion module 14, which is coupled to a CCD CCU 16. In a conventional system the image sensor would be coupled directly to the CCU, however they would have to be compatible with each other. Therefore, only a CMOS image sensor would be operable with a CMOS CCU, and only a CCD image sensor would be operable with a CCD CCU. By way of the presently described conversion module 14, this restriction is removed. As shown in FIG. 1, a conversion module 14 can be inserted between the image sensor 12 and the CCU 16 in order to allow a CMOS image sensor 12 to be used with a CCD CCU 16.

Conversion module 14 includes a D/A converter 20 to convert digital signals to analog signals. The D/A converter receives digital signals from CMOS image sensor 12 and converts these digital signals to analog signals, similar to the analog signals that are generated by a CCD image sensor.

Conversion module 14 also includes power circuitry 22 for providing power to the CMOS image sensor 12. The CMOS image sensor 12 has different power requirements than the power requirements of a CCD image sensor. In order for the CMOS image sensor 12 to function properly, it requires the appropriate power which is provided by power circuitry 22 of conversion module 14.

Conversion module 14 further includes clock circuitry 24 for providing one or more clock signals to the CMOS image sensor 12. Also shown is a clock generator 26 for providing a clock source utilized by clock circuitry 24. The CMOS image sensor 12 has different clock requirements than the clock requirements of a CCD image sensor. In order for the CMOS image sensor 12 to function properly, it requires the appropriate clock signaling which is provided by clock circuitry 24 of conversion module 14.

The CCD CCU 16 captures and processes the analog video signals from the conversion module 14 for display on a monitor, as well as for transfer to existing recording and printing devices. From the perspective of the CCD CCU 16, it appears as though a CMOS image sensor is being used.

Figure 2:
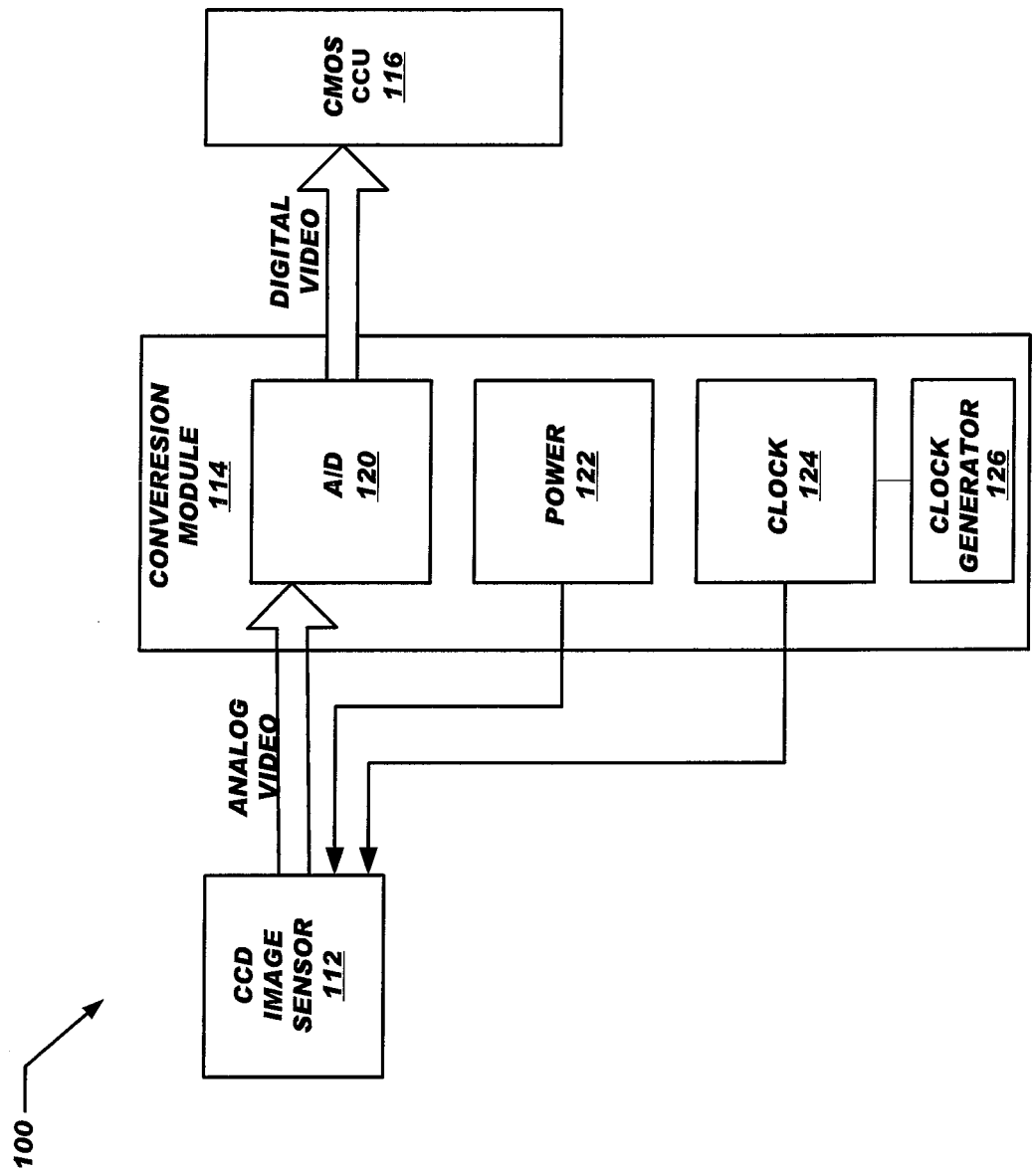
FIG. 2 is a block diagram of a conversion module for a CCD image sensor and a CMOS-based CCU in accordance with embodiments of the invention.

Referring now to FIG. 2, a second environment 100 including the use of a conversion module 114 as part of an endoscopic system is shown. A CCD image sensor 112 is shown coupled to conversion module 114, which is coupled to a CMOS CCU 116. In a conventional system the image sensor would be coupled directly to the CCU, however they would have to be compatible with each other. Therefore, only a CMOS image sensor would be operable with a CMOS CCU, and only a CCD image sensor would be operable with a CCD CCU. By way of the presently described conversion module 114, this restriction is removed. As shown in FIG. 2, a conversion module 114 can be inserted between the image sensor 112 and the CCU 116 in order to allow a CCD image sensor 112 to be used with a CMOS CCU 116.

Conversion module 114 includes an A/D converter 120 to convert analog signals to digital signals. The A/D converter 120 receives analog signals from CCD image sensor 112 and converts these analog signals to digital signals, similar to the digital signals that are generated by a CMOS image sensor.

Conversion module 114 also includes power circuitry 122 for providing power to the CCD image sensor 112. The CCD image sensor 112 has different power requirements than the power requirements of a CMOS image sensor. In order for the CCD image sensor 112 to function properly, it requires the appropriate power which is provided by power circuitry 122 of conversion module 114.

Conversion module 114 further includes clock circuitry 124 for providing one or more clock signals to the CCD image sensor 112. Also shown is a clock generator 126 for providing a clock source utilized by clock circuitry 124. The CCD image sensor 112 has different clock requirements than the clock requirements of a CMOS image sensor. In order for the CCD image sensor 112 to function properly, it requires the appropriate clock signaling which is provided by clock circuitry 124 of conversion module 114.

The CMOS CCU 116 captures and processes the digital video signals from the conversion module 114 for display on a monitor, as well as for transfer to existing recording and printing devices. From the perspective of the CMOS CCU 116, it appears as though a CCD image sensor is being used.

Figure 3A:
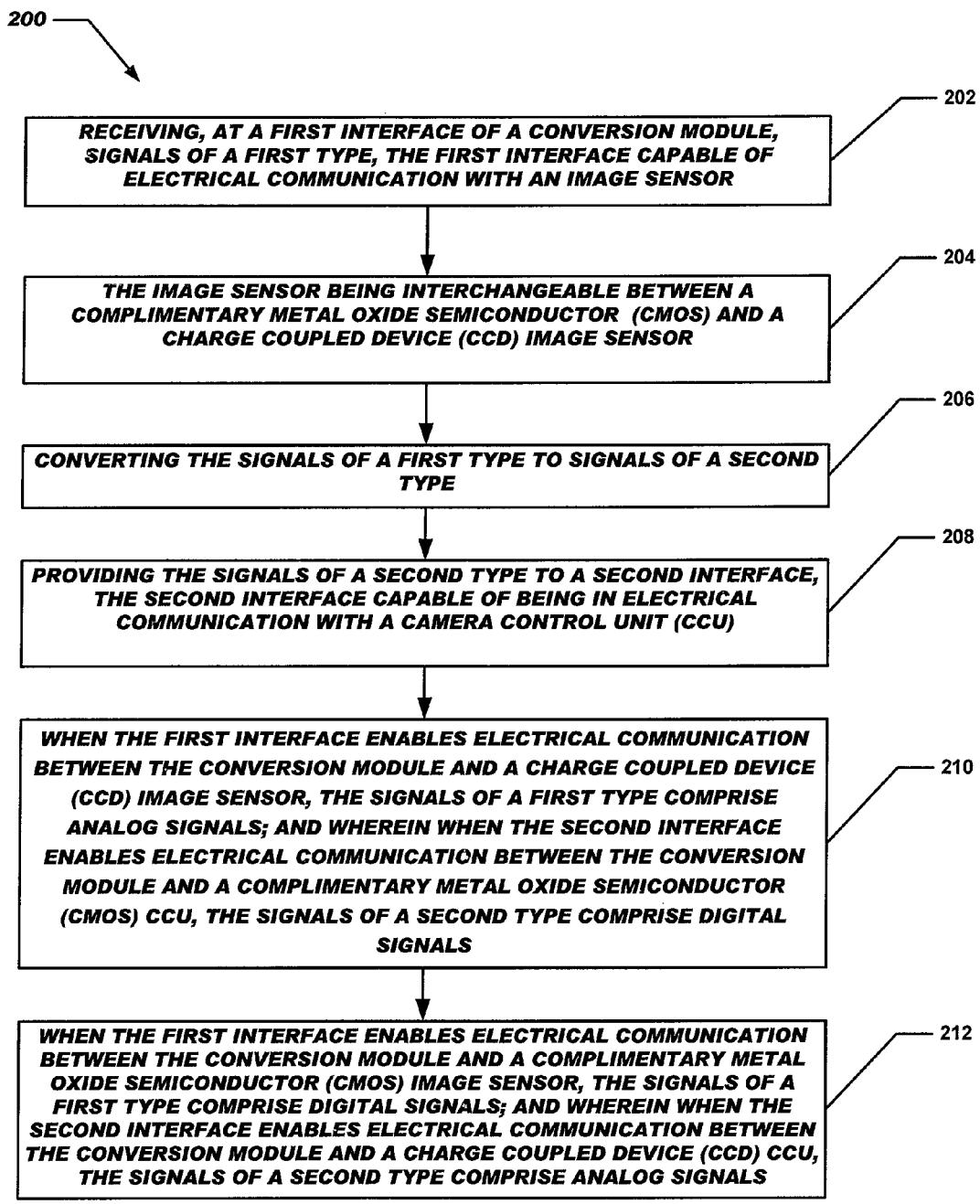

A flow chart of a particular embodiment of the presently disclosed method 200 is depicted in FIGS. 3A and 3B. The rectangular elements are herein denoted "processing blocks" and represent computer software instructions or groups of instructions. Alternatively, the processing blocks represent steps performed by functionally equivalent circuits such as a digital signal processor circuit or an application specific integrated circuit (ASIC). The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order.

In a particular embodiment, method 200 begins with processing block 202 which discloses receiving, at a first interface of a conversion module, signals of a first type, said first interface capable of electrical communication with an image sensor. The signal type depends on the image sensor being used. For a CCD image sensor the signal type is analog while for a CMOS image sensor the signal type is digital. Processing block 204 states the image sensor is interchangeable between a Complimentary Metal Oxide Semiconductor (CMOS) and a Charge Coupled Device (CCD) image sensor.

Processing block 206 recites converting the signals of a first type to signals of a second type. When the first type of signal comprises an analog signal, the signal is converted to a digital signal. Similarly, when the first type of signal is a digital signal, the signal is converted to an analog signal.

Processing block 208 discloses providing the signals of a second type to a second interface, the second interface capable of being in electrical communication with a Camera Control Unit (CCU). The CCU is designed to handle the second type of signals. The use of a conversion module allows a CCD image sensor to be used with a CMOS based CCU, and a CMOS image sensor to be used with a CCD based CCU. The module circuitry allows direct substitution of a CCD sensor in a CMOS based CCU imaging products and a CMOS sensor into existing CCD based products.

Processing block 210 states when the first interface enables electrical communication between the conversion module and a Charge Coupled Device (CCD) image sensor, the signals of a first type comprise analog signals; and wherein when the second interface enables electrical communication between the conversion module and a Complimentary Metal Oxide Semiconductor (CMOS) CCU, the signals of a second type comprise digital signals. This applies to a first embodiment of the conversion module wherein the conversion module is used with a CCD image sensor and a CMOS CCU.

Processing block 212 discloses when the first interface enables electrical communication between the conversion module and a Complimentary Metal Oxide Semiconductor (CMOS) image sensor, the signals of a first type comprise digital signals; and wherein when the second interface enables electrical communication between the conversion module and a Charge Coupled Device (CCD) CCU, the signals of a second type comprise analog signals. This applies to a second embodiment of the conversion module wherein the conversion module is used with a CMOS image sensor and a CCD CCU.

Processing continues with processing block 214 which states when the first interface enables electrical communication between the conversion module and a Charge Coupled Device (CCD) image sensor, the signals of a first type comprise analog signals and wherein when the second interface enables electrical communication between the conversion module and a Complimentary Metal Oxide Semiconductor (CMOS) CCU, the signals of a second type comprise digital signals; and wherein when the first interface enables electrical communication between the conversion module and a Complimentary Metal Oxide Semiconductor (CMOS) image sensor, the signals of a first type comprise digital signals; and wherein when the second interface enables electrical communication between the conversion module and a Charge Coupled Device (CCD) CCU, the signals of a second type comprise analog signals. This applies to a third embodiment of the conversion module wherein the conversion module can be used with a CCD image sensor and a CMOS CCU or with a CMOS image sensor and a CCD CCU Processing block 216 discloses wherein the converting is performed by conversion circuitry comprising: an Analog-to-Digital (A/D) converter in communication with the first interface and the second interface; timing circuitry in communication with the A/D converter and the first interface; and power circuitry for providing power to the A/D converter, the timing circuitry and the first interface. This relates to the first embodiment of the conversion module.

Processing block 218 states wherein the converting is provided by conversion circuitry comprising: a Digital-to-Analog (D/A) converter in communication with the first interface and the second interface; timing circuitry in communication with the D/A converter and the first interface; and power circuitry for providing power to the D/A converter, the timing circuitry and the first interface. This relates to the second embodiment of the conversion module.

Processing block 220 recites wherein the converting is provided by conversion circuitry comprising: an Analog-to-Digital (A/D) converter in communication with the first interface and the second interface; a Digital-to-Analog (D/A) converter in communication with the first interface and the second interface; timing circuitry in communication with the A/D converter, the D/A converter and the first interface; and power circuitry for providing power to the A/D converter, the D/A converter, the timing circuitry, and the first interface. This relates to the third embodiment of the conversion module.

As described above, the presently disclosed method and apparatus allows for conversion of signals from a first type of image sensor to a second type of camera control unit. The method and apparatus includes utilization of a conversion module that allows a CCD image sensor to be used with a CMOS based CCU, and a CMOS image sensor to be used with a CCD based CCU. This allows direct substitution of a CCD sensor in a CMOS based CCU imaging products and a CMOS sensor into existing CCD based products.

The device(s) or computer systems that integrate with the processor(s) may include, for example, a personal computer(s), workstation(s) (e.g., Sun, HP), personal digital assistant(s) (PDA(s)), handheld device(s) such as cellular telephone(s), laptop(s), handheld computer(s), or another device(s) capable of being integrated with a processor(s) that may operate as provided herein. Accordingly, the devices provided herein are not exhaustive and are provided for illustration and not limitation.

References to "a microprocessor" and "a processor", or "the microprocessor" and "the processor," may be understood to include one or more microprocessors that may communicate in a stand-alone and/or a distributed environment(s), and may thus be configured to communicate via wired or wireless communications with other processors, where such one or more processor may be configured to operate on one or more processor-controlled devices that may be similar or different devices. Use of such "microprocessor" or "processor" terminology may thus also be understood to include a central processing unit, an arithmetic logic unit, an application-specific integrated circuit (IC), and/or a task engine, with such examples provided for illustration and not limitation.

Furthermore, references to memory, unless otherwise specified, may include one or more processor-readable and accessible memory elements and/or components that may be internal to the processor-controlled device, external to the processor-controlled device, and/or may be accessed via a wired or wireless network using a variety of communications protocols, and unless otherwise specified, may be arranged to include a combination of external and internal memory devices, where such memory may be contiguous and/or partitioned based on the application. Accordingly, references to a database may be understood to include one or more memory associations, where such references may include commercially available database products (e.g., SQL, Informix, Oracle) and also proprietary databases, and may also include other structures for associating memory such as links, queues, graphs, trees, with such structures provided for illustration and not limitation.

References to a network, unless provided otherwise, may include one or more intranets and/or the Internet, as well as a virtual network. References herein to microprocessor instructions or microprocessor-executable instructions, in accordance with the above, may be understood to include programmable hardware.

Unless otherwise stated, use of the word "substantially" may be construed to include a precise relationship, condition, arrangement, orientation, and/or other characteristic, and deviations thereof as understood by one of ordinary skill in the art, to the extent that such deviations do not materially affect the disclosed methods and systems.

Throughout the entirety of the present disclosure, use of the articles "a" or "an" to modify a noun may be understood to be used for convenience and to include one, or more than one of the modified noun, unless otherwise specifically stated.

Elements, components, modules, and/or parts thereof that are described and/or otherwise portrayed through the figures to communicate with, be associated with, and/or be based on, something else, may be understood to so communicate, be associated with, and or be based on in a direct and/or indirect manner, unless otherwise stipulated herein.

Although the methods and systems have been described relative to a specific embodiment thereof, they are not so limited. Obviously many modifications and variations may become apparent in light of the above teachings. Many additional changes in the details, materials, and arrangement of parts, herein described and illustrated, may be made by those skilled in the art.

Having described preferred embodiments of the invention it will now become apparent to those of ordinary skill in the art that other embodiments incorporating these concepts may be used. Additionally, the software included as part of the invention may be embodied in a computer program product that includes a computer useable medium. For example, such a computer usable medium can include a readable memory device, such as a hard drive device, a CD-ROM, a DVD-ROM, or a computer diskette, having computer readable program code segments stored thereon. The computer readable medium can also include a communications link, either optical, wired, or wireless, having program code segments carried thereon as digital or analog signals. Accordingly, it is submitted that that the invention should not be limited to the described embodiments but rather should be limited only by the spirit and scope of the appended claims.

What is claimed is:

1. A conversion module comprising:
   a first interface for enabling electrical communication between said conversion module and an image sensor;
   said image sensor being interchangeable between a Complimentary Metal Oxide Semiconductor (CMOS) and a Charge Coupled Device (CCD) image sensor;
   a second interface for enabling electrical communication between said conversion module and a camera control unit (CCU); and
   conversion circuitry in communication with said first interface and said second interface, said conversion circuitry receiving signals of a first type from said first interface and being of a first stream type or a second stream type, converting said signals of a first type to signals of a second type, formatting the received signals to suit the CCU, and providing said signals of a second type to said second interface, the second interface interchangeable between connection to a CCD based CCU and a CMOS based CCU;
   the conversion circuitry further including:
   an Analog-to-Digital (A/D) converter in a first data path and in communication with said first interface and said second interface;
   a Digital-to-Analog (D/A) converter in a second data path and in communication with said first interface and said second interface;
   a controller for directing the first type signal to either the first data path or the second data path based on the image sensor type being CCD or CMOS, respectively;
   timing circuitry in communication with said A/D converter, said D/A converter and said first interface; and
   power circuitry for providing power to said A/D converter, said D/A converter, said timing circuitry, and said first interface, the first data path for processing received signals of the first stream type and the second data path for processing received signal of the second stream type.

2. The conversion module of claim 1 wherein when said first interface enables electrical communication between said conversion module and a Charge Coupled Device (CCD) image sensor, said signals of a first type comprise analog signals; and wherein when said second interface enables electrical communication between said conversion module and a Complimentary Metal Oxide Semiconductor (CMOS) CCU, said signals of a second type comprise digital signals.

3. The conversion module of claim 1 wherein when said first interface enables electrical communication between said conversion module and a Complimentary Metal Oxide Semiconductor (CMOS) image sensor, said signals of a first type comprise digital signals; and wherein when said second interface enables electrical communication between said conversion module and a Charge Coupled Device (CCD) CCU, said signals of a second type comprise analog signals.

4. The conversion module of claim 2 wherein said conversion circuitry comprises:
an Analog-to-Digital (A/D) converter in communication with said first interface and said second interface;
timing circuitry in communication with said A/D converter and said first interface; and
power circuitry for providing power to said A/D converter, said timing circuitry and said first interface.

5. The conversion module of claim 3 wherein said conversion circuitry comprises:
a Digital-to-Analog (D/A) converter in communication with said first interface and said second interface;
timing circuitry in communication with said D/A converter and said first interface; and
power circuitry for providing power to said D/A converter, said timing circuitry and said first interface.

6. The conversion module of claim 1 wherein when said first interface enables electrical communication between said conversion module and a Charge Coupled Device (CCD) image sensor, said signals of a first type comprise analog signals; and wherein when said second interface enables electrical communication between said conversion module and a Complimentary Metal Oxide Semiconductor (CMOS) CCU, said signals of a second type comprise digital signals.

7. The conversion module of claim 1 wherein when said first interface enables electrical communication between said conversion module and a Complimentary Metal Oxide Semiconductor (CMOS) image sensor, said signals of a first type comprise digital signals; and wherein when said second interface enables electrical communication between said conversion module and a Charge Coupled Device (CCD) CCU, said signals of a second type comprise analog signals.

8. A method comprising:
receiving, at a first interface of a conversion module, signals of a first type and being of a first stream type or a second stream type, said first interface capable of electrical communication with an image sensor;
said image sensor being interchangeable between a Complimentary Metal Oxide Semiconductor (CMOS) and a Charge Coupled Device (CCD) image sensor;
converting said signals of a first type to signals of a second type, the converting performed by at least one of an Analog-to-Digital (A/D) or a Digital-to-Analog (D/A) converter in communication with said first interface and said second interface, timing circuitry in communication with said converter and said first interface, and power circuitry for providing power to said A/D converter, said D/A converter, said timing circuitry, and said first interface, said converting provided by conversion circuitry comprising:

an Analog-to-Digital (A/D) converter in a first data path and in communication with said first interface and said second interface;
a Digital-to-Analog (D/A) converter in a second data path and in communication with said first interface and said second interface;
a controller for directing the first type signal to either the first data path or the second data path based on the image sensor type being CCD or CMOS, respectively;
timing circuitry in communication with said A/D converter, said D/A converter and said first interface; and
power circuitry for providing power to said A/D converter, said D/A converter-, said timing circuitry, and said first interface; and
providing said signals of a second type to a second interface of the conversion module, said second interface capable of being in electrical communication with a Camera Control Unit (CCU), formatting the received signals to suit the CCU, the second interface interchangeable between connection to a CCD based CCU and a CMOS based CCU, the first data path for processing received signals of the first stream type and the second data path for processing received signals of the second stream type.

9. The method of claim 8 wherein when said first interface enables electrical communication between said conversion module and a Charge Coupled Device (CCD) image sensor, said signals of a first type comprise analog signals; and wherein when said second interface enables electrical communication between said conversion module and a Complimentary Metal Oxide Semiconductor (CMOS) CCU, said signals of a second type comprise digital signals.

10. The method of claim 8 wherein when said first interface enables electrical communication between said conversion module and a Complimentary Metal Oxide Semiconductor (CMOS) image sensor, said signals of a first type comprise digital signals; and wherein when said second interface enables electrical communication between said conversion module and a Charge Coupled Device (CCD) CCU, said signals of a second type comprise analog signals.

11. The method of claim 8 wherein when said first interface enables electrical communication between said conversion module and a Charge Coupled Device (CCD) image sensor, said signals of a first type comprise analog signals and wherein when said second interface enables electrical communication between said conversion module and a Complimentary Metal Oxide Semiconductor (CMOS) CCU, said signals of a second type comprise digital signals; and wherein when said first interface enables electrical communication between said conversion module and a Complimentary Metal Oxide Semiconductor (CMOS) image sensor, said signals of a first type comprise digital signals; and wherein when said second interface enables electrical communication between said conversion module and a Charge Coupled Device (CCD) CCU, said signals of a second type comprise analog signals.

12. The conversion module of claim 1 wherein the second interface is configured for switchable display types, the switchable display types accommodating at least one of CCD (Charge Coupled Device) generated signals and CMOS (Complimentary Metal Oxide Semiconductor) generated signals.

13. A method comprising:
receiving, at a first interface of a conversion module, signals of a first type and being of a first stream type or a second stream type, said first interface capable of electrical communication with an image sensor;

said image sensor being interchangeable between a Complimentary Metal Oxide Semiconductor (CMOS) and a Charge Coupled Device (CCD) image sensor;

converting said signals of a first type to signals of a second type, said converting provided by conversion circuitry comprising:
- an Analog-to-Digital (A/D) converter in a first data path and in communication with said first interface and said second interface;
- a Digital-to-Analog (D/A) converter in a second data path and in communication with said first interface and said second interface;
- a controller for directing the first type signal to either the first data path or the second data path based on the image sensor type being CCD or CMOS, respectively;
- timing circuitry in communication with said A/D converter, said D/A converter and said first interface; and
- power circuitry for providing power to said A/D converter, said D/A converter, said timing circuitry, and said first interface;

providing said signals of a second type to a second interface of the conversion module, said second interface capable of being in electrical communication with a Camera Control Unit (CCU), the second interface configured for switchable display types, the switchable display types accommodating at least one of CCD (Charge Coupled Device) generated signals and CMOS (Complimentary Metal Oxide Semiconductor) generated signals; and formatting the received signals to suit the CCU, the second interface interchangeable between connection to a CCD based CCU and a CMOS based CCU, the first data path for processing received signals of the first stream type and the second data path for processing received signals of the second stream type.

14. The conversion module of claim 1, wherein the conversion module is configured to be disposed between the image sensor and the CCU distal from the image sensor.

15. The method of claim 8 further comprising switching, at the second interface, wherein the second interface is configured for switchable display types, the switchable display types accommodating at least one of CCD (Charge Coupled Device) generated signals and CMOS (Complimentary Metal Oxide Semiconductor) generated signals.

16. The conversion module of claim 1 wherein the first data path and the second data path are defined by different physical connections of the first interface and operable to direct the received signals to the first data path or the second data path based on which physical connection is engaged for receiving the signals of the first type.

17. The conversion module of claim 1 wherein the conversion module includes selection logic operable for detecting an incoming stream of a first stream type or a second stream type, and directing the received signals to the first or second data paths, respectively.

18. The conversion module of claim 1 wherein the conversion module includes an FPGA (Field Programmable Gate Array) for identifying a coding scheme expected by the second interface and providing the second type signals corresponding to the identified coding scheme.

19. The conversion module of claim 1 wherein the conversion module further comprises an FPGA (Field Programmable Gate Array) for detecting whether the first type signals correspond to the first stream type or the second stream type and adjusting a power level provided via the first interface based on the first type signals.

20. The conversion module of claim 1 wherein the conversion module further comprises clock circuitry and is operable for detecting whether the first type signals correspond to the first stream type or the second stream type and providing a clock signal to the first interface based on the detected first type signals.

21. The conversion module of claim 1 wherein the first and second interfaces are defined by physical temporary plug connections for connection to an imaging product via the first interface and a vision system via the second interface.

* * * * *